US007509253B2

(12) United States Patent
Luckett

(10) Patent No.: US 7,509,253 B2
(45) Date of Patent: Mar. 24, 2009

(54) DEVICE FOR DETERMINING LATENCY BETWEEN STIMULUS AND RESPONSE

(76) Inventor: Joseph C. Luckett, P.O. Box 982, Daytona Beach, FL (US) 32115

( * ) Notice: Subject to any disclaimer, the term of this patent is extended or adjusted under 35 U.S.C. 154(b) by 257 days.

(21) Appl. No.: 11/493,408

(22) Filed: Jul. 26, 2006

(65) Prior Publication Data

US 2008/0027728 A1 Jan. 31, 2008

(51) Int. Cl.
*G10L 19/14* (2006.01)
*G10L 11/00* (2006.01)
*A61B 19/00* (2006.01)
*A61B 5/12* (2006.01)

(52) U.S. Cl. ....................... 704/211; 704/270; 600/557; 73/585

(58) Field of Classification Search ....................... None
See application file for complete search history.

(56) References Cited

U.S. PATENT DOCUMENTS 4,166,452 A * 9/1979 Generales, Jr. .............. 600/554
4,201,225 A 5/1980 Bethea, III et al.
4,377,158 A * 3/1983 Friedman et al. ............ 128/897
4,502,489 A * 3/1985 Alston, Jr. ................... 600/559
4,637,402 A 1/1987 Adelman
5,193,058 A * 3/1993 Bassili et al. ............... 434/321
5,230,629 A * 7/1993 Buschke ...................... 434/236
5,876,334 A * 3/1999 Levy .......................... 600/300
6,086,541 A 7/2000 Rho
6,157,913 A * 12/2000 Bernstein .................... 704/275
6,160,893 A 12/2000 Saunders et al.
6,379,314 B1 4/2002 Horn
6,416,485 B1 * 7/2002 Rovetta et al. .............. 600/595
6,506,164 B2 1/2003 Reischl et al.
6,522,988 B1 2/2003 Hou
6,524,258 B1 2/2003 Sturzebecher et al.
7,198,605 B2 * 4/2007 Donofrio et al. ............ 600/559

* cited by examiner

*Primary Examiner*—David R Hudspeth
*Assistant Examiner*—Brian L Albertalli
(74) *Attorney, Agent, or Firm*—J. Wiley Horton

(57) ABSTRACT

A device which uses an input of speech and measures latency between stimulus and response. The device generally includes an input transducer for converting a stimulus speech sound into an electrical signal and transmits the electrical signal to an electric circuit. In the preferred embodiment, the electric circuit includes a central processing unit which utilizes delay time counters to measure the length of time between signals. A second input transducer is used to convert a response speech sound into an electrical signal and transmits the electrical signal to the electric circuit. Each input transducer operates on a separate channel, so that the central processing unit may easily distinguish between stimulus sounds and response sounds.

12 Claims, 5 Drawing Sheets

DEVICE FOR DETERMINING LATENCY BETWEEN STIMULUS AND RESPONSE

BACKGROUND OF THE INVENTION

1. Field of the Invention

This invention relates to the field of speech-measuring devices. More specifically, the present invention comprises a device which takes an input of speech and measures the time lapse or latency between the stimulus and response.

2. Description of the Related Art

Being able to determine the "latency" of an individual's response to a speech stimulus is significant in many fields including audiology, speech pathology, psychometry, and motor testing of all kinds. For example, one theory holds that the longer it takes someone to perceive a speech unit correctly, the less clear or focused their perception is. Inversely, the shorter the temporal latency between stimulus and response, the higher the quality the perceptive event at the moment of perception is. This theory is based on the well-studied strong central component of psycho-acoustic ability. Short latency indicates "quickness of response" in auditory perception, cognitive recognition, and other aspects relevant to human measurement. Accordingly, it would be beneficial to have a device that is capable of accurately measuring the latency between an auditory stimulus and an individual's response.

BRIEF SUMMARY OF THE INVENTION

The present invention comprises a micro-controller based device which uses an input of speech and measures latency between stimulus and response. The device generally includes an input transducer for converting a stimulus speech sound into an electrical signal and transmitting the electrical signal to an electric circuit. A second input transducer is used to convert a response speech sound into an electrical signal and transmit the electrical signal to the electric circuit. In the preferred embodiment, the electric circuit includes a central processing unit which utilizes delay time counters to measure the length of time between signals. Each input transducer operates on a separate channel, so that the central processing unit may easily distinguish between stimulus sounds and response sounds.

REFERENCE NUMERALS IN THE DRAWINGS

Figure 1A:
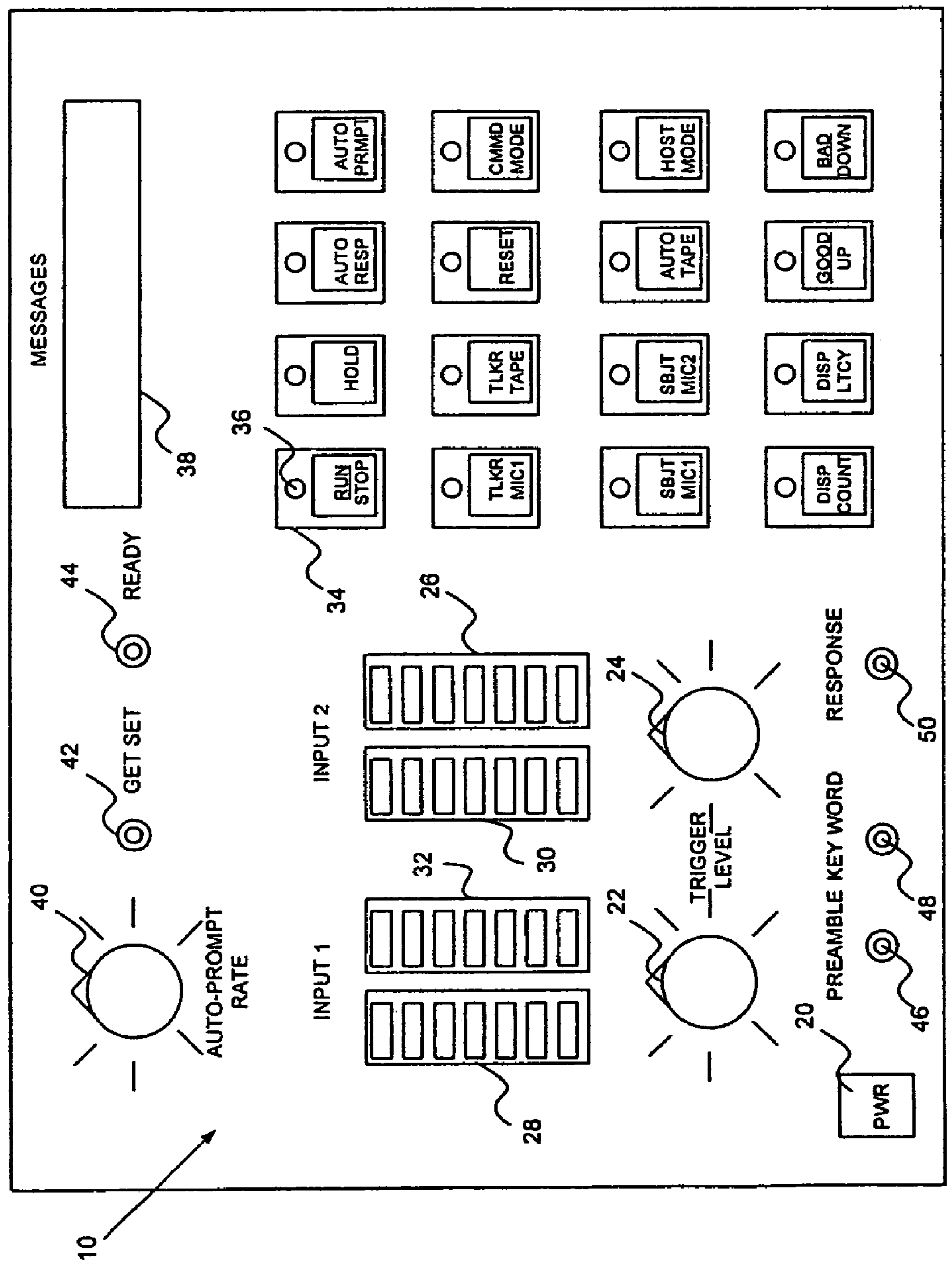
FIG. 1A is a top view, illustrating a control panel used in the present invention.

| | | | |
|---|---|---|---|
| 10 | latency measuring device | 12 | input transducer |
| 14 | input transducer | 16 | A/D converter |
| 18 | central processing unit | 20 | power button |
| 22 | trigger level adjustment | 24 | trigger level adjustment |
| 26 | input level indicator | 28 | input level indicator |
| 30 | trigger level indicator | 32 | trigger level indicator |
| 34 | run/stop command button | 36 | command button LED |
| 38 | message screen | 40 | auto prompt rate adjustment |
| 42 | "get set" LED | 44 | "ready" LED |
| 46 | preamble LED | 48 | key word LED |
| 50 | response LED | 52 | gain adjustment |
| 54 | gain adjustment | 56 | talker microphone jack |
| 58 | subject microphone jack | 60 | audio in jack |
| 62 | earphone out jack | 64 | computer serial port |
| 66 | audio player | 68 | alternate response source |
| 70 | audio in jack | 72 | microphone one jack |
| 74 | microphone two jack | 76 | auxiliary in jack |
| 78 | preamplifier | 80 | talker input |
| 82 | preamplifier | 84 | response input |
| 86 | multiplexer | 88 | metronome rate adjustment |
| 90 | trigger level adjustment | 92 | trigger level adjustment |
| 94 | metronome | 96 | post-amplifier |
| 98 | Channel One output | 100 | mixing amplifier |
| 102 | audior recorder output | 104 | Channel Two output |
| 106 | earphone output | 108 | "ready" LED |
| 110 | "get set" LED | 112 | audio recorder start/stop |
| 114 | message display | 116 | program |
| 118 | memory | 120 | lamps |
| 122 | bad test command button | 124 | good test command button |
| 126 | automatic good/bad determiner | 128 | talker mic/audio command buttons |
| 130 | run/idle command buttons | 132 | audio manual/auto command buttons |
| 134 | select mic1/mic2 command buttons | 136 | test/command command buttons |
| 138 | metro/auto push buttons | 140 | metronome clock signal |
| 142 | white LED signal | 144 | green LED signal |
| 146 | metronome signal | 148 | time interval |
| 150 | ready signal | 152 | window signal |
| 154 | Channel Two trigger level | 156 | Channel Two signal |
| 158 | Channel One trigger level | 160 | Channel One signal |

-continued

| REFERENCE NUMERALS IN THE DRAWINGS | | | |
|---|---|---|---|
| 162 | sample exceeds trigger function | 164 | Channel One trigger |
| 166 | short delay | 168 | short delay |
| 170 | Channel One end | 172 | Channel Two trigger |
| 174 | Channel Two start | 176 | good test end |
| 178 | failed test end | 180 | count/latency display buttons |
| 182 | transmission path | 184 | transmission path |

DETAILED DESCRIPTION OF THE INVENTION

FIG. 1A shows a control panel used in the present invention, latency measuring device 10. The preferred embodiment of the present invention generally comprises a series of delay timers which measure the "timing out" of a series of timer-clock circuits. Short timers are used to measure the differences in delay between the phonemic elements within a word. For example, the words "street" has nearly imperceptible pauses which occur between the "s" and the "tree" and the final "t".

In a hearing aid evaluation, a speech discrimination test utilizes a series of words to test speech understanding. In this test, the tester says something such as "Say the word . . . street." The ellipsis is used in the present case to denote a short pause between the word "word" and the word "street." In this test, the subject responds with the word he or she understands. A long delay timer is set to time a delay between the preparatory phrase "say the word" and the test word "street." Another long delay timer measures the time between the stimulus and the response of the subject.

It should be noted that the "test word" (in the above example, "street") may be replaced by a picture representing the test word. For example, the test word "street" may be shown to the subject either in text form or as a picture of a street. The subject may either repeat the test word they perceive or touch a picture on an electronic touchpad. If an electronic touchpad is used, the subject may be presented with an array of pictures with the "correct answer picture" included in the array. Accordingly, the present invention may be used for many different subject populations including pediatric populations or people who cannot verbalize responses.

Figure 1B:
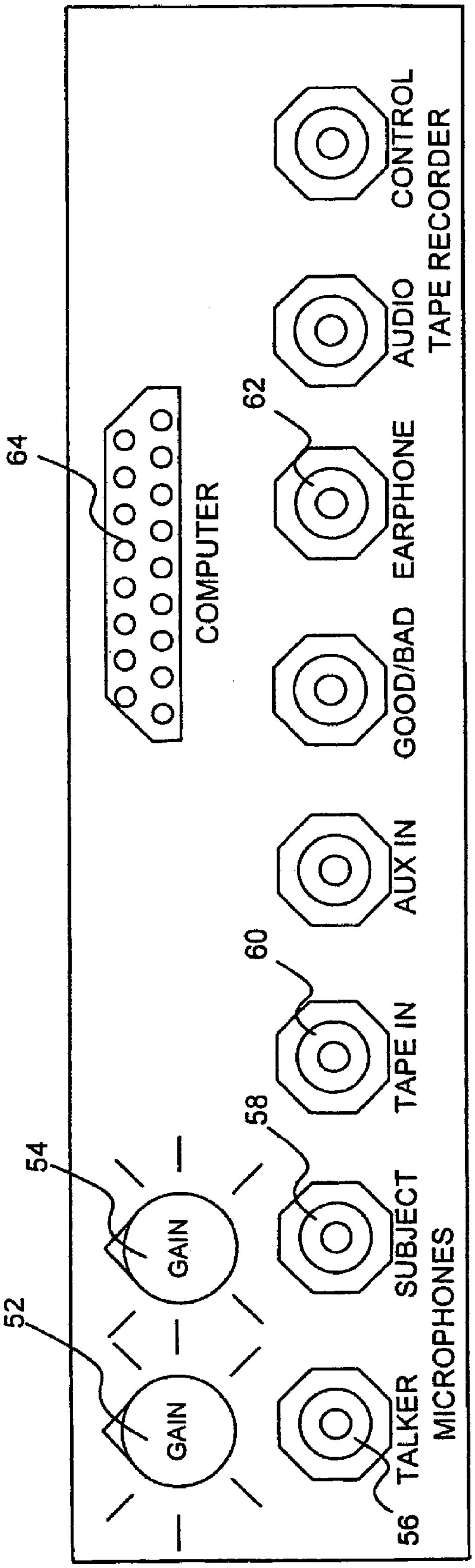
FIG. 1B is a back view, illustrating the input/output panel of the present invention.

Latency measuring device 10 may be provided in many forms. For example, the device might be a stand-alone unit as illustrated in FIG. 1A and FIG. 1B. Alternatively, the device may interface with a personal computer (with the control settings being made by mouse clicks, as an example).

The aforementioned delay timers are activated by a trigger circuit which operates on a "one-shot" type algorithm imbedded in the firmware of the circuit. The trigger circuit only responds to signals which "spike" or "flicker" above a preprogrammed target voltage. The target voltage may be set above the background noise by the tester using a sensitivity potentiometer, adjustable noise gate, or computer-setting. The trigger circuit begins the first delay timer at the onset of the speech input (in the aforementioned example, when the tester says "Say"). An amber signal light may be provided to indicate that the trigger circuit has been activated and the tester may begin the test.

Figure 2:
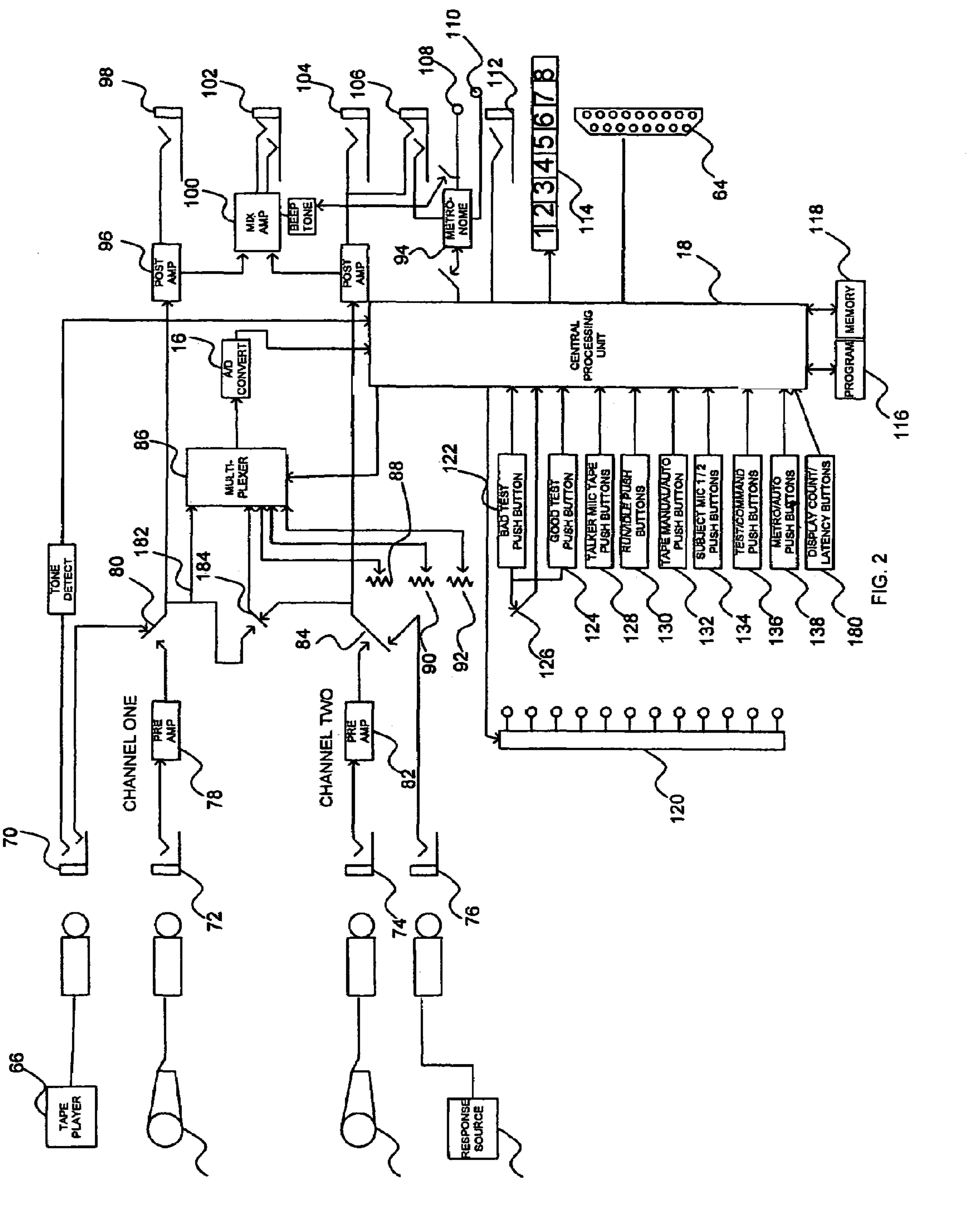
FIG. 2 is a schematic, illustrating the present invention.

FIG. 2 shows the signal flow in the device. Input transducer 12 transmits the speech stimulus to Channel One. From Channel One, the signal is converted from analog to digital using A/D converter 16. Input transducer 14 transmits a speech response to Channel Two, where the signal is again converted from analog to digital using A/D converter 16. Digital signals from Channel One and Channel Two are then transmitted to central processing unit 18 for analysis of temporal and amplitude aspects of the signals.

Central processing unit 18 monitors Channel One for a stimulus signal which exceeds the trigger level. Channel One is then monitored for longer time intervals. Central processing unit 18 observes Channel One for the actual cessation of trigger-level signals. Accordingly, a short delay timer rapidly samples Channel One to know when speech begins and a long delay timer samples at longer time intervals to determine the "cessation of speech." The cessation of speech is noted by a separate timer or system clock. The system clock counts down at a set rate from an arbitrary maximum value. The current countdown value corresponding with the cessation of speech is stored in memory associated with central processing unit 18 for future comparison.

Central processing unit 18 then begins monitoring for the response on Channel Two. Initially, central processing unit 18 monitors Channel Two rapidly with a short delay timer. When a speech response is detected over the trigger level, central processing unit 18 stores the time of the onset of the response relative to the current value of the system clock in the memory associated with central processing unit 18. In addition, the cessation of speech on Channel Two may also be noted using the long delay timers (as used in Channel One) when the trigger level is no longer exceeded. Central processing unit 18 may store the current value of the system clock corresponding to the cessation of speech on Channel Two in the memory.

If the system clock registered a value of 10000 at the cessation of speech on Channel One, and a value of 5000 when the onset of speech is observed on Channel Two, a total of 5000 time units would have elapsed between the two points. If each unit of time on the system clock corresponds to 5 microseconds, then 5000 time units equates to a real time latency of 25 milliseconds between stimulus and response.

In addition, the calculations may be further refined to take into account the length of time it takes for the stimulus to reach the subject's ear after leaving the speaker's mouth. For example, by entering the distance of the speaker to the subject, the device can calculate the time it takes for speech to travel from the speaker to the subject by dividing the distance between the speaker and subject by the speed of sound. Accordingly, if the speaker is 10 feet from the listener, the time it takes for speech to reach the subject is 9 milliseconds (since sound travels at approximately 1100 feet per second). This value may be subtracted from the measured latency to determine the actual latency. In the previous example, 9 milliseconds should be subtracted from the measured latency of 25 milliseconds to obtain the actual latency of 16 milliseconds.

An alternate embodiment of the present invention utilizes a recorded stimulus instead of a live speaker. In this case, the stimulus may be played through earphones, making the aforementioned distance factor calculation moot.

In some cases it may be important to control the metronome-rate or rhythm at which the speech stimulus is provided. Different color lights, such as green and white, may be employed on the device to assist the administrator of the test in controlling the rhythm. For example, the device may flash a green light at the onset of speech to indicate that the trigger level of speech has been observed by central processing unit 18. A white light may then flash contemporaneously with or just after the stimulus word is stated by the test administrator. The green light may then flash again indicating the expectation of the onset of the response. The white light may then be configured to flash again when the subject provides the response. A variable window of time may then be set by the device or the administrator before the administrator is to provide the next stimulus.

In the previous example, the green lights may be either voice activated or may occur at a set metronome rate to indicate to the test administrator when and how to keep within the rhythm of the test (if rendered by live voice). For prerecorded test stimuli, the metronome rate for the delivery of the test stimuli may also be integrated with the recorded stimuli. In this case, the green and white lights may become indicators of the metronome rate of the recorded stimulus as well. Using this feature, the time intervals between and among the various stimuli and response, as well as the intervals of time between the stimuli themselves can be measured and/or varied as needed.

The device may also be programmed to wait on the response whether it occurs within the prescribed tempo of the test or not. Alternatively, the device may be programmed to deliver stimuli at a set rate regardless of the response. Using an "automatic" mode, whereby the metronome rate of the test is set to a "relentless" rate (where the stimulus presentation rate and inter stimulus rate are pre-set), the response may be judged as "incorrect" if it does not occur within the prescribed temporal interval between the stimuli. A red light may also flash to indicate a failed response.

With the general features and functionalities of the present invention in mind, the particulars of the preferred embodiment may now be considered in greater detail. FIG. 1A and FIG. 1B show a possible configuration for latency measuring device 10. A top view of latency measuring device 10 is shown in FIG. 1A.

The user of the device may user trigger level adjustment 22 to set the trigger level for the input transducer or microphone which corresponds to input one/Channel One. Another trigger level adjustment 24 is provided to set the trigger level for the input transducer to input two/Channel Two. In the present example, Channel One corresponds to the test administrator's microphone and Channel Two corresponds to the test subject's microphone. Trigger level adjustment 22 and trigger level adjustment 24 are used to calibrate the device so that the device may differentiate stimuli and responses from background noise. Accordingly, the trigger levels should be set just above background noise levels but below the normal speech sound levels. Trigger level indicator 30 and trigger level indicator 32 are provided so that the user may see where the trigger levels are set in relation to the signals transmitted via Channel Two and Channel One respectively. Input level indicator 26 and input level indicator 28 illustrate the intensity of the signal that is currently being transmitted in Channel Two and Channel One respectively. These allow the user to visually set the appropriate trigger level.

A series of command buttons are provided so that the user may utilize the various functions of the device. For example, run/stop command button 34 is provided for activating the latency measuring program. Each command button also has command button LED 36 which indicates the status of each function. The LEDs that appear on the command buttons are not necessarily directly controlled by the switch corresponding to the command button. For example, run/stop command button 34 is pressed to start a test run. After the processor determines that it is prepared to run the test, the LED on the button is lit. If the processor determines that something is wrong, the LED stays dark and a message is displayed in message screen 38. Power button 20 is also provided for powering up the device.

The back of the device is illustrated in FIG. 1B. Gain adjustment 52 and gain adjustment 54 are used to amplify the stimulus and response signals respectively. The amount of gain provided to each signal may be adjusted by turning the appropriate knob. A series of input jacks are also provided along the back of the device so that it can be connected to various input transducers and auxiliary sources. Talker microphone jack 56 is provided for the test administrator's microphone and subject microphone jack 58 is provided for the test subject's microphone. In addition, audio in jack 60 is provided so that a prerecorded stimulus may be played. Earphone out jack 62 may be used for connecting earphones. Earphones may be used by the subject if a prerecorded stimulus is used or if the stimulus is provided by a live test administrator. Computer serial port 64, which may also be a USB port, is provided so that the device may interface with a personal computer for enhanced analysis and storage.

The schematic illustrating the circuitry of the preferred embodiment of the present invention is provided in FIG. 2. Input transducer 12 and input transducer 14 are the principal inputs to the device. Input transducer 12 is connected to microphone one jack 72, which transmits signals from input transducer 12 to Channel One. Input transducer 14 is connected microphone two jack 74, which transmits signals from input transducer 14 to Channel Two. The signals from input transducer 12 and input transducer 14 are amplified by preamplifier 78 and preamplifier 82 respectively. Preamplifiers 78 and 82 may be adjusted by gain adjustments 52 and 54 as described previously. Once amplified, the stimulus signal is transmitted to talker input 80 and the response signal is transmitted to response input 84. If a prerecorded stimulus is used, audio player 66 may be connected to the device via audio in jack 70. The prerecorded stimulus signal is transmitted to Channel One via talker input 80.

In addition, alternate response source 68 may be provided if the test subject is to provide a nonverbal response to the stimulus. For example, the subject may be asked to press a button when the test administrator says the name of a type of animal. Alternate response source 68 may be connected to the device at auxiliary in jack 76 and the alternate response source signal is transmitted to Channel Two via response input 84.

From talker input 80, the stimulus signal is split. One signal is sent to Channel One output 98 (after amplification by post-amplifier 96) and the other signal is sent to multiplexer 86 via transmission path 182. Likewise, from response input 84, the response signal is split. One signal is sent to Channel Two output 104 (after amplification by a post-amplifier) and the other signal is sent to multiplexer 86 via transmission path 184. In addition to being sent to Channel Two output 104, the response signal is also transmitted to earphone output 106. Although it is not illustrated in FIG. 2, the stimulus signal may also be sent to earphone output 106 in addition to being sent to Channel One output 98 similar to the response signal.

Multiplexer 86 also receives as its inputs metronome rate adjustment 88 (which is adjusted by the user with auto prompt rate adjustment 40 shown in FIG. 1A), trigger level adjustment 90 (corresponding to trigger level adjustment 22 in FIG. 1A), and trigger level adjustment 92 (corresponding to trigger level adjustment 24 in FIG. 1A). Multiplexer 86 transmits the signals to A/D converter 16 where the signals are converted from analog to digital. From A/D converter 16, the signals are transmitted to central processing unit 18.

The stimulus signals and response signals along with other information transmitted from multiplexer 86 is analyzed by central processing unit 18. The operating instructions for central processing unit 18 are provided in object code format from program 116 which is stored in memory associated with central processing unit 18. The analysis of the stimulus signals, response signals, and latency therebetween is performed using the method that was generally described previously. This method will be described in greater detail subsequently.

Central processing unit 18 utilizes memory 118 for storing relative time values for response and stimulus signals and other information needed for its analysis. Central processing unit 18 can transmit data regarding the response and stimulus signals to a personal computer via computer serial port 64 (shown in FIG. 1B) for further analysis or storage. Universal Serial Bus ("USB") type connections may also be provided for increased comparability. In addition, central processing unit 18 can display information about the response and stimulus via message display 114. Although numeric symbols are illustrated in FIG. 2, message display 114 may be configured to display other symbols as well.

Central processing unit 18 also communicates with metronome 94. Metronome 94 may both be used as an internal clock for the device and may be used to provide rhythm signals to the test administrator or prerecorded stimulus feed to prompt the stimuli. When used as an internal clock, metronome 94 acts as an input to central processing unit 18 so that central processing unit 18 may associate the various transmitted signals with relative time. Metronome 94 may provide this rhythm information to the test administrator via "ready" LED 108 (corresponding to "ready" LED 44 in FIG. 1A) and "get set" LED 110 (corresponding to "get set" LED 42 in FIG. 1A). These lamps act to prompt the test administrator when to deliver the stimuli to the test subject.

Central processing unit 18 also communicates with audio player 66 or other device used to provide prerecorded stimuli. Central processing unit 18 may be configured to either start audio player 66 when the administrator selects to run the program, or it may be configured to start and stop the device providing the prerecorded stimuli at various times based on the program. Although reference has been made to a audio player in the current example, the reader will appreciate that compact discs or other mediums which are configured to play recorded sounds may also be used.

Central processing unit 18 may create an audio copy of the test for archive purposes. If this function is desired, central processing unit 18 operates audio recorder start/stop 112 to begin and end recording. The audio recorder records the test via a signal feed from audio recorder output 102. Audio recorder output 102 receives its input from mixing amplifier 100. Mixing amplifier mixes the stimulus signals received from Channel One, the response signals received from Channel Two, along with a beep tone provided by metronome 94 (where the beep tone corresponds to the prompt of "ready" LED 108).

The series of command buttons illustrated in FIG. 1A also interface with central processing unit 18 as illustrated in FIG. 2. For example, the test administrator may press bad test command button 122 if the subject responds incorrectly to the stimulus. If the subject responds correctly, the administrator may press good test command button 124. Central processing unit 18 associates these command button inputs with the signals it receives and registers the signals in memory 118. If the subject fails to respond to the stimulus in a set period of time, central processing unit 18 may determine that the test was failed utilizing automatic good/bad determiner 126. In addition, central processing unit 18 interfaces with talker mic/audio command buttons 128 (which inform central processing unit 18 the input source of the stimulus), run/idle command buttons 130 (which inform central processing unit 18 when the administrator is ready to begin and pause the test), audio manual/auto command buttons 132, select mic1/mic2 command buttons 134, test/command command buttons 136, metro/auto push buttons 138, and count/latency display buttons 180 (which prompt central processing unit 18 to display count and latency information in message screen 38). In turn, central processing unit 18 activates lamps 120 (corresponding to various command button LEDs 36) and analyzes the test as prescribed by program 116.

Figure 3:
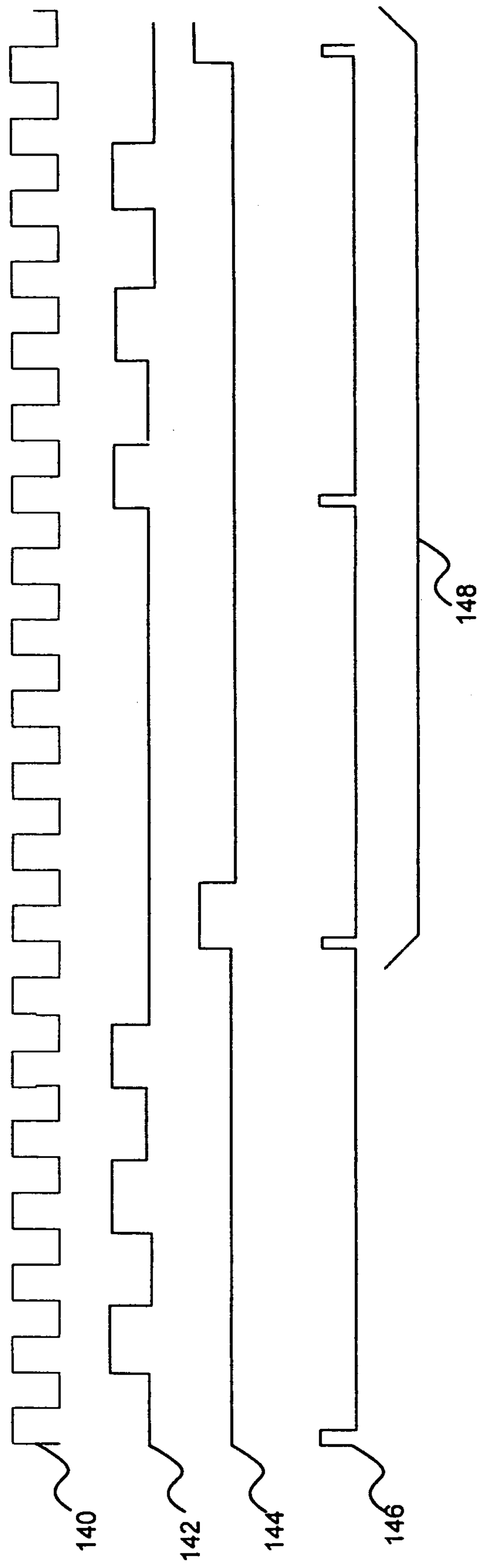
FIG. 3 is a transmission signal diagram, illustrating the present invention.
Figure 4:
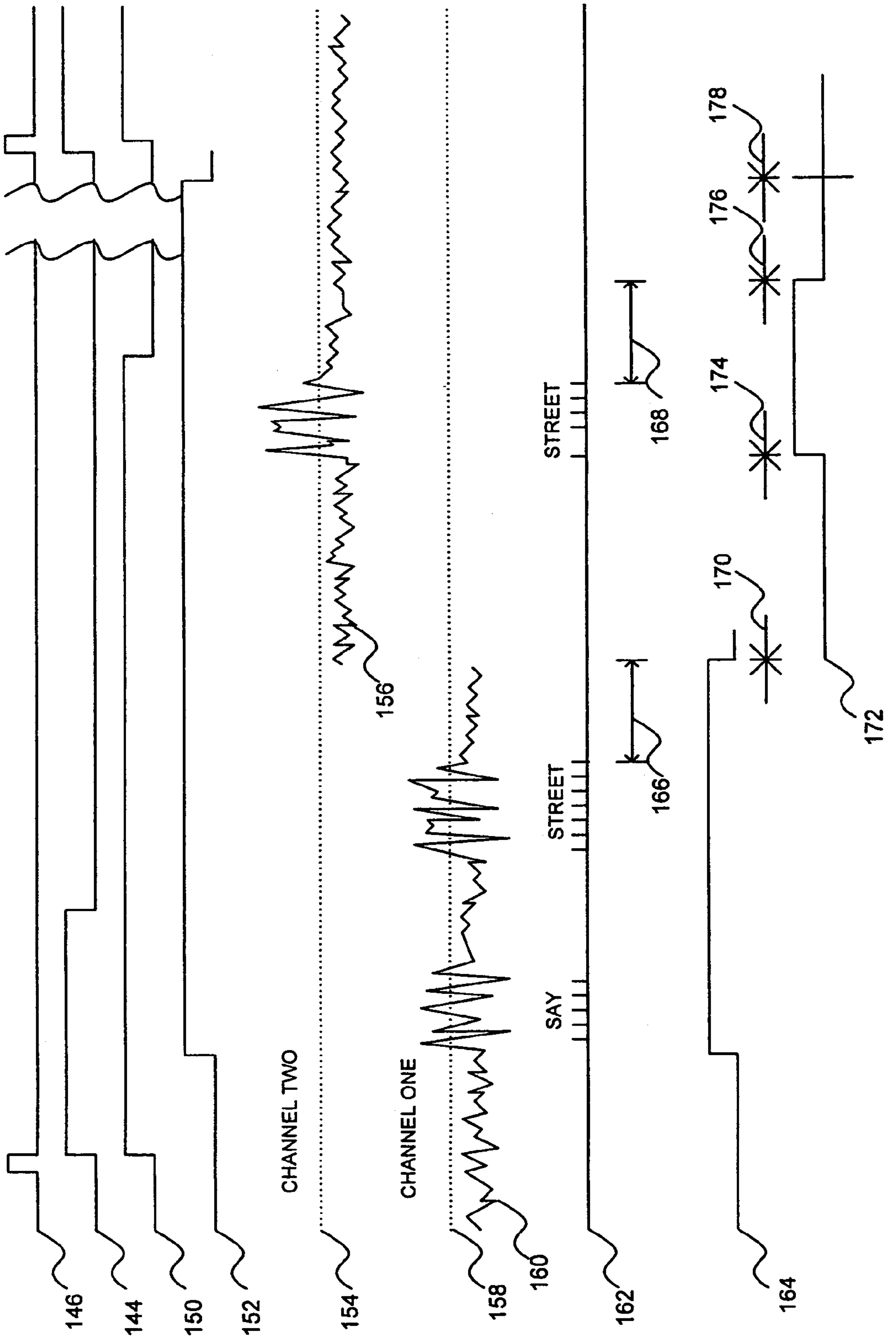
FIG. 4 is a transmission signal diagram, illustrating the present invention.

Transmission signal diagrams illustrating the device's rhythm and time keeping functions are provided in FIGS. 3 and 4. As illustrated in FIG. 3, metronome clock signal 140 oscillates periodically at a very short time interval. The metronome clock sets the minimum time between tests. White LED signal 142 causes "get set" LED 42 to flash three times in close succession. This prompts the test administrator to prepare to deliver the stimulus. After, white LED signal 142 flashes three times, green LED signal 144 causes "ready" LED 44 to flash once. "Ready" LED 44 indicates that the device is prepared for the administrator to begin the test. Metronome signal 146 represents the rhythm of metronome 94. As shown in FIG. 3, metronome 94 maintains a periodic signal based on metronome clock signal 140.

A sample of a test is provided in FIG. 4 to illustrate the time-keeping and the latency-analysis functionalities of the device. Time interval 148 from FIG. 3 is reproduced in part in FIG. 4. Activity on both channels is ignored until the device is "ready." The "ready" state is indicated by the flash of "ready" LED 44 corresponding to green LED signal 144. The device stays in the ready state for a period of time as signified by ready signal 150.

The first sample on Channel One that exceeds the trigger level starts the sampling process and begins the long delay (triggers long delay timer). As illustrated in FIG. 4, Channel One signal 160 exceeds Channel One trigger level 158 when the administrator says the word "say." Sample exceeds trigger function 162 illustrates the instances where the sampling process detects an "above trigger level" signal. Each sample exceeding the trigger level continues the long delay. This delay time should be long enough to cover any natural pauses during and between words. Also, window signal 152 is started when Channel One signal 160 first exceeds Channel One trigger level 158. Window signal 152 defines a period of time for the test. Any response falling outside window signal 152 may be designated a "failed" test.

Also, when the long delay timer times out, the next sample on Channel One starts the short delay time (short delay 166). This delay time is only long enough to cover any natural pauses within a word. When the short delay times out, the relative time of the time out is registered in memory 118 for the cessation of speech on Channel One. This also causes the sampling process to switch to Channel Two.

The first sample on Channel Two that exceeds the trigger level starts the long delay again. As illustrated in FIG. 4, Channel Two signal 156 exceeds Channel Two trigger level 154 when the subject says the word "street." After the administrator says the first "street", any sample exceeding the trigger level continues the delay. When Channel Two signal 156 exceeds Channel Two trigger level 154, the relative time is stored in memory 118 and associated with the onset of speech on Channel Two. When the short delay times out (short delay 168), the relative time of the time out is registered in memory 118 for the cessation of speech on Channel Two. This also clears the ready signal 150.

If the end of the "ready" period is beyond the end of the "window" period, that test is failed and no data is saved and no calculations are made. If the "ready" period overlaps a metronome pulse, that metronome pulse is "lost" and the device waits for the next metronome pulse to restart the "ready" period.

The analysis and measurement of latency will now be considered in greater detail. Channel One trigger 164 illustrates the time period of "activity" on Channel One. Channel One end 170 signifies the point in time where sampling ceases on Channel One and is switched to Channel Two. Channel Two trigger 172 illustrates the time period of "activity" on Channel Two. Channel Two start 174 corresponds to the onset of speech on Channel Two and good test end 176 indicates the end of "activity" on Channel Two. The example test provided in FIG. 4 is a "good" test because the response was provided in the "window" period. If the response does not occur prior to failed test end 178, the test is "failed" as described previously.

The reader will note that the period of activity include the last short delay before cessation of speech was acknowledged. These periods of time are illustrated in FIG. 4 as short delay 166 and short delay 168. Accordingly, subtracting the delay time from the cessation of speech times which were registered in memory 118 gives the actual times of the last sample of each channel.

"Latency" may be measured from different perspectives. In one example, latency may be determined as follows: (1) subtract the time of short delay 166 from the cessation of speech time (Channel One end 170) registered for the cessation of speech on Channel One; (2) subtract that value from the relative time stored for the onset of speech on Channel Two (Channel Two start 174). This measurement of latency describes the amount of time between the cessation of the stimulus to the onset of the response. Latency may also measured from the cessation of the stimulus to the cessation of the response. This calculation may be made by subtracting the two values of cessation of speech registered for each channel since the short delay period is constant (Good test end 176 minus Channel One end 170). All latency times and test results may be saved in memory 118 (which may be RAM). The results may optionally be displayed on message screen 38.

The preceding description contains significant detail regarding the novel aspects of the present invention. It should not be construed, however, as limiting the scope of the invention but rather as providing illustrations of the preferred embodiments of the invention. As an example, the device may be entirely implemented on a personal computer. For example, analogous measurement and analysis logic may be programmed onto the test administrator's computer. The stimulus and response signals may also be illustrated on the computer screen. This enables the test administrator to capture the stimulus and response waveforms for more detailed analysis. Such a variation would not alter the function of the invention. Thus, the scope of the invention should be fixed by the following claims, rather than by the examples given.

Having described my invention, I claim:

1. A device for measuring latency in a human subject between an audible stimulus and a human speech response, comprising:

a. an audible stimulus monitoring channel for monitoring an audible stimulus audible by said human subject, wherein the cessation of said audible stimulus occurs at a first time, said first time being determined by a detector capable of monitoring the onset of said audible stimulus and determining when said audible stimulus falls below a specified trigger level, thereby indicating said cessation of said audible stimulus;

b. memory means for storing said first time;

c. a human speech transducer, configured to detect the initiation of said human speech response and transmit a response signal when said initiation of said human speech response is detected at a second time; and d. computation means for computing said latency between said second time and said first time.

2. The device of claim 1, wherein said detector includes a sampling means configured to detect the initiation of said human speech response, said sampling means configured to identify said onset of said human speech response when said response signal exceeds a trigger level.

3. The device of said claim 2, said sampling means including a short delay timer having a delay period duration only long enough to cover natural pauses within a word.

4. The device of claim 2, said sampling means further including a long delay timer having a delay period duration long enough to cover any natural pauses during and between words.

5. The device of claim 2, further comprising a registering means configured to register said first time in said memory means when said cessation of said audible stimulus occurs.

6. The device of claim 1, further comprising an internal clock for measuring relative time.

7. The device of claim 1, said detector including a long delay timer having a delay period duration long enough to cover any natural pauses during and between words.

8. The device of claim 1, further comprising a means for adjusting said specified trigger level.

9. A device for measuring latency between a stimulus and a response comprising:

a. an electronic circuit having
   i. a first channel configured to transmit a response signal corresponding to said response; and
   ii. an internal clock for measuring relative time;

b. an input transducer configured to detect said response and transmit said response as said response signal to said first channel of said electronic circuit;

c. a first means for rapidly sampling said first channel for the onset of said response signal, said first means configured to identify said onset of said response signal when said response signal exceeds a trigger level;

d. a means for registering the relative time of said onset of said response signal;

e. a second channel with a second channel monitoring means configured to identify the onset of said stimulus when a signal produced by said stimulus exceeds a trigger level and to identify the cessation of said stimulus when said stimulus signal fails to exceed said trigger level;

f. means for registering the relative time of said cessation of said stimulus; and g. computation means for determining said latency between said cessation of said stimulus and said response.

10. A device for measuring latency between a stimulus and a response comprising:

a. an electronic circuit having i. a first channel configured to transmit a response signal corresponding to said response;

ii. a second channel configured to transmit a stimulus signal corresponding to said stimulus;

iii. a clock for measuring relative time;

iv. a signal sampler, said signal sampler configured to rapidly sample said first channel for the onset of said response signal, said signal sampler configured to identify said onset of said response signal when said response signal exceeds a trigger level;

v. a register configured to store the relative time of said onset of said response signal when identified by said signal sampler;

b. an input transducer configured to detect said response and transmit said response as said response signal to said first channel of said electronic circuit; and c. said signal sampler configured to rapidly sample said second channel for the onset of said stimulus signal, said signal sampler configured to identify said onset of said stimulus signal when said response signal exceeds a second trigger level;

d. said signal sampler configured to rapidly sample said second channel for the cessation of said stimulus signal, said signal sampler configured to identify said cessation of said stimulus when the signals transmitted through said second channel fail to exceed said second trigger level for a specified period of time; and e. wherein said register is further configured to store the relative time of said cessation of said stimulus signal when identified by said signal sampler.

11. The device of claim 10 further comprising a central processing unit configured to computing the latency between said cessation of said stimulus signal and said onset of said response signal.

12. A device for measuring latency between a stimulus and a response comprising:

f. an electronic circuit having i. a first channel configured to transmit a response signal corresponding to said response;

ii. a second channel configured to transmit a stimulus signal corresponding to said stimulus;

iii. a clock for measuring relative time;

g. a memory unit for storing information regarding said stimulus signal and said response signal;

h. a central processing unit for analyzing said response signal and said stimulus signal and measuring the latency therebetween, said central processing unit configured to measure said latency by i. sampling said second channel for the onset of said stimulus, said onset of said stimulus corresponding to a first point in time when a sample of said stimulus signal exceeds a trigger level;

ii. sampling said second channel for the cessation of said stimulus after said onset of said stimulus has been determined, said cessation of said stimulus corresponding to a second point in time when the signals transmitted through said second channel fail to exceed said trigger level for a specified period of time;

iii. registering the relative time of said second point in time corresponding to said cessation of said stimulus in said memory unit;

iv. sampling said first channel for the onset of said response, said onset of said response corresponding to a third point in time when a sample of said response signal exceeds a second trigger level;

v. registering the relative time of said third point in time corresponding to said onset of said response in said memory unit; and i. an input transducer configured to detect said response and transmit said response as said response signal to said first channel of said electronic circuit.

* * * * *